United States Patent [19]

Holtkamp, Sr.

[11] Patent Number: Plant 6,108

[45] Date of Patent: Feb. 16, 1988

[54] AFRICAN VIOLET PLANT NAMED ACADIA

[75] Inventor: Reinhold Holtkamp, Sr., Isselburg, Fed. Rep. of Germany

[73] Assignee: Gesellschaftsvertrag uber die Erfindergemeinschaft "OPTIMARA", Rees Haffen, Fed. Rep. of Germany

[21] Appl. No.: 823,515

[22] Filed: Jan. 28, 1986

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

An African violet plant named Acadia having semi-double flowers and violet-blue flower color; strong, upright flower stems, each of which carries 8–10 or more flowers; vigorous growth habit, producing a saleable plant 9–10 weeks after potting; full, tight flower head well above the leaves, and long-lasting, non-dropping flowers.

1 Drawing Figure

The present invention comprises a new and distinct cultivar of African violet plant, botanically known as *Saintpaulia ionantha*, and hereinafter referred to by the cultivar name Acadia.

The new cultivar was originated from a cross made in a controlled breeding program in Isselburg, West Germany. The female, or seed parent was a cultivar designated C81/1, a light blue cultivar. The male, or pollen parent was a cultivar designated D219/3, a cultivar having pink frilled semi-double flowers.

Acadia was discovered and selected by me as a flowering plant within the progeny of the stated cross in a controlled environment in Isselburg, West Germany. Asexual reproduction of the new cultivar by leaf cuttings, as performed by me at Isselburg, West Germany, has demonstrated that the combination of characteristics as herein disclosed for the new cultivar are firmly fixed and retained through successive generations of asexual reproduction.

Acadia has not been observed under all possible environmental conditions. The phenotype may vary significantly with variations in environment such as temperature, light intensity and day length. The following observations, measurements and values describe the new cultivar as grown in Isselburg, West Germany and Nashville, Tenn. under greenhouse conditions which closely approximate those generally used in commercial practice.

The following traits have been repeatedly observed and are determined to be basic characteristics of Acadia which in combination distinguish this African violet as a new and distinct cultivar:

1. Strong, upright flower stems curving toward the center.
2. First flash of flowers form a tight bouquet above the leaves.
3. The flowers are violet-blue and are typically semi-double, with many additional flower petals, and the anthers are still clearly visable.
4. Each plant carries up to 8 and more upright flower stems, each of which carries 8–10 or more flowers.
5. Vigorous grower.
6. Plant is saleable 9 to 10 weeks after potting.
7. Medium green velvet leaves, slightly hairy and heavily indented.
8. Long lasting, non-dropping flowers.

9. Seed capsule pushes slightly through.
10. Three to four anthers composed of two anther cells.
11. The flowers have frilled and waved edges.
12. After maturity, the flowers dry off, and remain on the peduncle without becoming infected by botrytis.

The accompanying photographic drawing shows a typical specimen plant of the new cultivar grown in a 4" pot. The colors appearing in the photograph are as true as possible with color illustrations of this type.

In the following description, color references are made to The Royal Horticultural Society Colour Chart (RHS), except where general colors of ordinary significance are referred to. Color values were taken under natural light conditions at approximately 2:00 p.m. in Nashville, Tenn.

Botanical classification: *Saintpaulia ionantha*, Ramat., cv. Acadia.

Parentage:

*Male parent.*—D219/3.

*Female parent.*—C81/1.

PROPAGATION

The new cultivar holds its distinguishing characteristics through successive propagations by leaf cuttings.

PLANT

From 8 cm. to 10 cm. tall when grown in pots, and approximately 25–35 cm. in diameter when fully grown.

Leaves:

*Shape.*—Simple, round to heart-shaped.

*Diameter.*—70–80 mm. wide.

*Texture.*—Velvety, heavy indentation.

*Ribs and veins.*—Under side, well pronounced, bright green and shiny; bright green between the veins.

*Color (upper side).*—Yellow-green 147A, with tinge of brown.

*Color (Under side).*—Yellow-green 148C.

*Petioles.*—Strong, upright, brown-green; hairy.

Flowers:

*Buds.*—Size: 8–10 mm. before opening. Shape: Ball-shaped. Color: Greenish-brown.

*Sepals.*—Shape: Spear-shaped, hairy; five in number. Color: Greenish-brown.

*Calyx.*—Funnel-shaped, basifixed.

*Peduncle.*—Length: Relatively short. Character: Strong, upright, hairy. Color: Brownish.

Individual flowers:

*Size.*—30–35 mm. in diameter.

*Shape.*—Semi-double.

*Color (upper side).*—Violet-blue, 94B-C.

*Color (under side).*—Violet-blue, 91B-C. Under relatively cool conditions and more intensive light, the flower color tends to intensify.

*Borne.*—Each flower stem carries 8–12 flowers on a strong, upright peduncle.

Flowering habit: A tight bouquet is formed well above the leaves, with a saleable plant being produced in a 4" pot in 9–10 weeks after potting a small plantlet.

Reproductive organs:

*Stamens.*—2 to 3.

*Anthers.*—2 to 3, each with two anther cells.

*Filaments.*—3–4 mm., yellow-purple.

*Styles.*—6 mm., light purple.

Roots: Normally developed, white when young, turning slightly brownish when older.

Disease resistance: Good.

General Observations

Acadia is a vigorous grower, with attractive velvet medium green leaves. Out of the center 10 and more stems are produced, each of which is strong, curved slightly toward the center, and carries 8–12 and more semi-double medium-blue flowers that are slightly waved and frilled. The flower has many additional flower petals, but the anther cells remain visible. The fully developed flower head forms a tight bouquet. Approximately 9–10 weeks after potting the plant is saleable, and the flowers are long-lasting and non-dropping.

I claim:

1. A new and distinct cultivar of African violet named Acadia, as illustrated and described, and particularly characterized by its semi-double flowers and violet-blue flower color; strong, upright flower stems, each of which carries 8–10 or more flowers; vigorous growth habit, producing a saleable plant 9–10 weeks after potting; full, tight flower head well above the leaves, and by its long-lasting, non-dropping flowers.

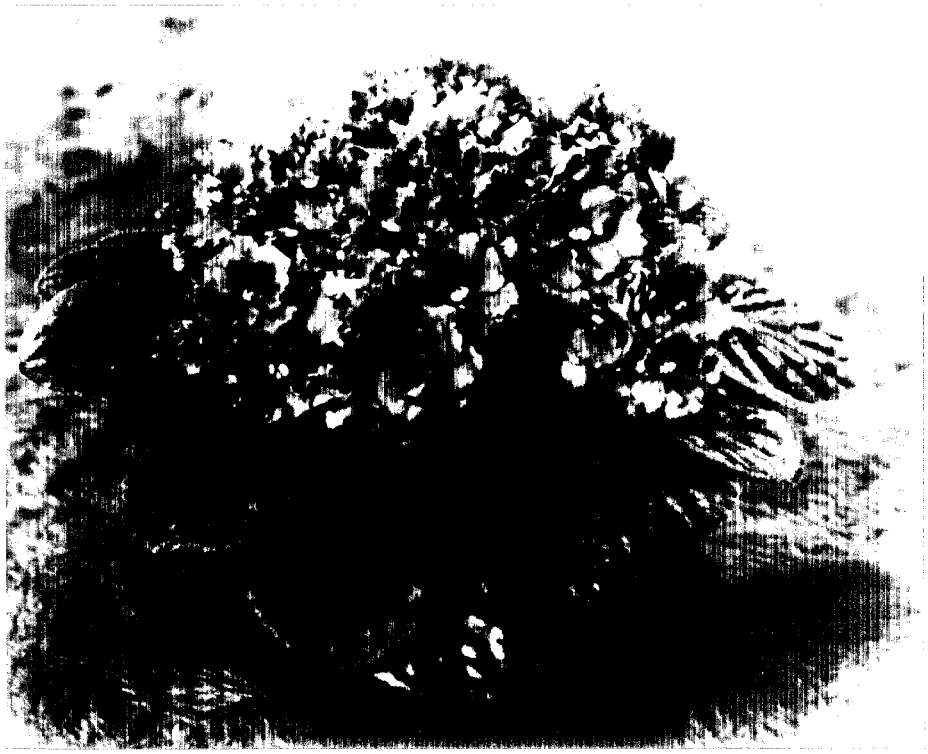

* * * * *